United States Patent [19]

Tsao

[11] 4,113,786
[45] Sep. 12, 1978

[54] HYDROGEN CHLORIDE RECOVERY

[75] Inventor: Utah Tsao, Jersey City, N.J.

[73] Assignee: The Lummus Company, Bloomfield, N.J.

[21] Appl. No.: 673,095

[22] Filed: Apr. 2, 1976

[51] Int. Cl.² .......................................... C07C 17/00
[52] U.S. Cl. ........................... 260/659 A; 260/654 A; 260/654 R; 260/659 R; 260/660; 260/662 A; 423/488
[58] Field of Search .......... 260/659 R, 662 A, 659 A, 260/654 A, 654 R, 660, 656 R; 423/488, 481; 55/71

[56] References Cited

U.S. PATENT DOCUMENTS

| 3,233,978 | 2/1966 | Alkemade | 423/488 |
| 3,453,073 | 7/1969 | Sims | 423/481 |
| 3,879,481 | 4/1975 | Sze et al. | 260/659 R |
| 3,968,050 | 7/1976 | Riegel | 260/662 A |

FOREIGN PATENT DOCUMENTS

| 770,533 | 10/1967 | Canada | 423/488 |
| 462,366 | 1/1950 | Canada | 423/481 |
| 1,009,574 | 11/1965 | United Kingdom | 55/71 |

*Primary Examiner*—Delbert E. Gantz
*Assistant Examiner*—Joseph A. Boska
*Attorney, Agent, or Firm*—Marn & Jangarathis

[57] ABSTRACT

Process for recovering hydrogen chloride from a gas withdrawn from an oxychlorination reaction zone which contains hydrogen chloride and water vapor wherein the gas is initially cooled, followed by contacting the gas with a small amount of water to absorb the hydrogen chloride from the gas. The water content is controlled to provide an aqueous hydrogen chloride stream having a hydrogen chloride concentration of from 10% to 20%, with the absorbed aqueous hydrogen chloride being recycled to the oxychlorination reaction. A dilute aqueous hydrogen chloride stream, obtained from another portion of the process, may be employed in the initial cooling step, as a direct quench, resulting in vaporization of the dilute aqueous hydrogen chloride stream and eliminating the necessity for a hydrogen chloride concentrator.

7 Claims, 1 Drawing Figure

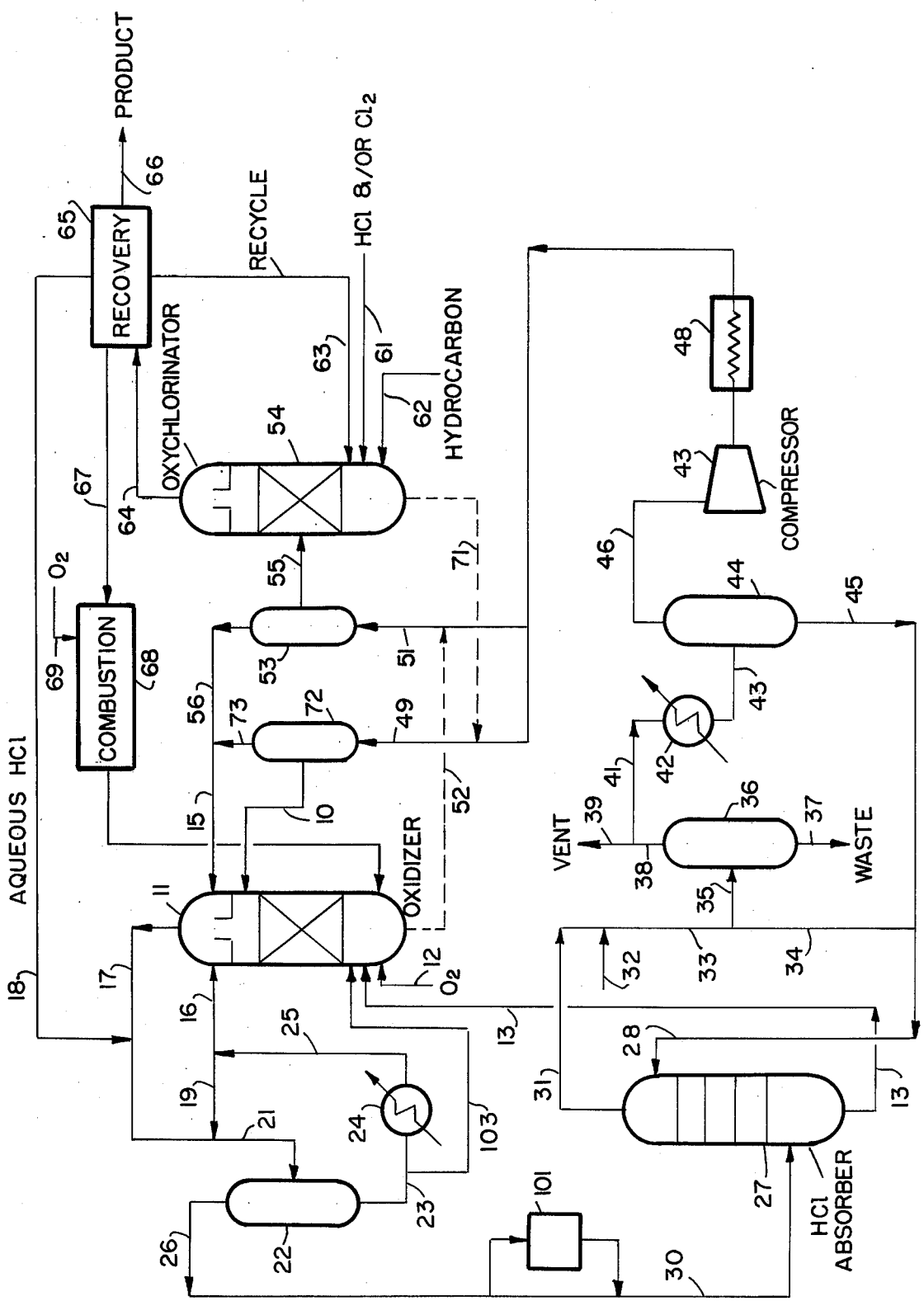

HYDROGEN CHLORIDE RECOVERY

This invention relates to hydrogen chloride recovery. More particularly, this invention relates to the recovery of hydrogen chloride from a gas recovered from an oxychlorination reaction. This invention further relates to the recovery of hydrogen chloride in a process for the production of chlorinated hydrocarbons.

Oxychlorination reactions using hydrogen chloride and oxygen are well known in the art. The effluent withdrawn from an oxychlorination process contains hydrogen chloride and water vapor and in many cases, the overall economics of the process may be dependent upon the effective recovery of such hydrogen chloride. In general, the hydrogen chloride is recovered from such effluents as a dilute aqueous hydrogen chloride solution, and in order to effectively utilize such hydrogen chloride, in most cases, the recovered aqueous hydrogen chloride solution must be concentrated. Accordingly, there is a need for effective recovery of hydrogen chloride from an oxychlorination effluent, which does not require a separate step for effecting concentration of recovered aqueous hydrogen chloride.

An object of this invention is to provide for improved recovery of hydrogen chloride.

Another object of this invention is to provide for recovery of hydrogen chloride from an oxychlorination reaction effluent containing water vapor and hydrogen chloride.

A further object of this invention is to provide for recovery of more concentrated aqueous hydrogen chloride solution from an oxychlorination reaction effluent gas.

These and other objects of the invention should be more readily apparent from reading the following detailed description thereof.

In accordance with the present invention, there is provided a process for recovering hydrogen chloride wherein a gas, containing hydrogen chloride and water vapor, which is withdrawn from an oxychlorination reactor, is cooled to a temperature of from about 250° to about 170° F, at a pressure of from 1 to about 20 atm. The cooled gas is then contacted with water to absorb hydrogen chloride from the gas, with the water being introduced in a quantity to provide an absorbed aqueous hydrogen chloride solution having a hydrogen chloride concentration of from 10% to 20%, by weight. The absorption is effected at a temperature of from 170° to 250° F (outlet gas temperature) to minimize condensation of water from the gas, whereby water produced in the oxychlorination reaction can be vented from the system in gaseous form.

In accordance with another aspect of the present invention, the gas containing hydrogen chloride and water vapor, is cooled prior to the absorption, by direct contact with a dilute aqueous hydrogen chloride solution obtained from another portion of the process to effect partial vaporization thereof and recover a more concentrated aqueous hydrogen chloride solution.

More particularly, the effluent withdrawn from the oxychlorination reaction, containing hydrogen chloride and water vapor, is cooled, as hereinabove described, to a temperature of from 250° to 170° F, preferably a temperature of from 220° to 170° F, at a pressure of from 1 to 20 atm, and preferably from 2 to 5 atm. The cooling is preferably effected by direct contact quenching, generally with an aqueous hydrogen chloride solution; however, it is to be understood that such cooling could be effected by other means, such as, for example, indirect cooling. As hereinabove described, in general, a portion of the cooling requirements can be provided by a dilute aqueous hydrogen chloride stream recovered from another portion of the process, which provides the added advantage of effecting recovery of a more concentrated aqueous hydrogen chloride solution.

Hydrogen chloride and water vapor is present in the cooled effluent in an amount whereby condensation would provide an aqueous hydrogen chloride solution containing no greater than 8%, by weight, hydrogen chloride, and generally in the order of from 1% to 6%, by weight, hydrogen chloride. In accordance with the present invention, hydrogen chloride is recovered from the effluent by absorption of hydrogen chloride at an elevated temperature to provide for recovery of a more concentrated hydrogen chloride solution and venting of water produced in the process in gaseous form.

The cooled effluent is then introduced into an absorber wherein hydrogen chloride present in the gas stream is absorbed by direct contact with water, employed as an absorbent. The absorption is effected in a manner such as to provide an absorbed hydrogen chloride stream having a hydrogen chloride concentration of from 10% to 20%, by weight. In this manner, the major portion of the water vapor, present in the effluent, is withdrawn, as a gas, from the absorber, thereby providing an absorbed hydrogen chloride stream, of increased concentration, for recycle to the oxychlorination reaction and permitting venting of the water from the system in gaseous form.

In general, the absorber is operated at a gas outlet temperature of from 170° to 250° F, preferably 175° to 225° F, and at a pressure of from 1 to 20 atm, and preferably from 2 to 5 atm. The water, as hereinabove described, is added in an amount to provide the desired hydrogen chloride concentration in the recovered aqueous hydrogen chloride stream. In general, the water is added in an amount to produce a hydrogen chloride solution of from 10% to 20%, by weight, hydrogen chloride.

The gas stream withdrawn from the absorber generally has a hydrogen chloride concentration of no greater than 0.01 mole %, and in general, the hydrogen chloride concentration is in the order of 0.0025 to 0.005 mole %. The hydrogen chloride present in such gas stream is neutralized, in gaseous form at the elevated temperature and a portion of the gas is vented to the atmosphere at the elevated temperature whereby water produced in the oxychlorination is vented without condensation thereof.

As hereinabove described, in accordance with another aspect of the present invention, a dilute aqueous hydrogen chloride stream is concentrated by employing the dilute aqueous hydrogen chloride containing stream as a quench liquid for cooling the effluent from the oxychlorination reaction. In general, the dilute aqueous hydrogen chloride stream has a hydrogen chloride concentration of no greater than 8%, most generally in the order of from 1% to 6%, all by weight. The aqueous hydrogen chloride is generally at a temperature of from 150° to 200° F. The dilute aqueous hydrogen chloride stream is partially vaporized as a result of the contact with the effluent to produce a more concentrated hydrogen chloride solution, generally in the order of 10% to 20%, by weight, hydrogen chloride.

The effluent containing hydrogen chloride and water vapor may be recovered from any one of a wide variety of oxychlorination reactions, and as representative examples of such oxychlorinations, there may be mentioned: (1) reaction between molecular oxygen, hydrogen chloride and a salt mixture of the higher and lower valent forms of a multivalent metal chloride to enrich the higher valent metal chloride content of the mixture; (2) reaction between molecular oxygen, hydrogen chloride and a hydrocarbon or a partially chlorinated hydrocarbon, generally a lower (1-4 carbon atoms) aliphatic hydrocarbon or partially chlorinated lower aliphatic hydrocarbon to produce a chlorinated hydrocarbon; (3) reaction between hydrogen chloride and oxygen to produce chlorine (generally referred to as a Deacon reaction, but for the purposes of this invention, this reaction is considered an oxychlorination); (4) reaction between an oxychloride of the multivalent metal and hydrogen chloride to produce the higher valent metal chloride; and (5) reaction between an oxychloride of a multivalent metal, hydrogen chloride and a hydrocarbon or partially chlorinated hydrocarbon to produce a chlorinated hydrocarbon.

This invention is particularly applicable to a process for producing chlorinated hydrocarbons by the use of a molten salt containing a multivalent metal chloride in its higher and lower valent state, generally manganese, iron, copper, cobalt or chromium, preferably copper. In such a process, the multivalent metal chloride is contacted with molecular oxygen and hydrogen chloride, generally as an aqueous solution thereof and/or gaseous hydrogen chloride, to enrich the higher valent metal chloride content of the molten salt mixture and to produce the oxychloride. The molten salt containing the oxychloride and the higher and lower valent metal chloride is then employed for the production of a chlorinated hydrocarbon. The process of the present invention is employed for recovering hydrogen chloride from the gas withdrawn from the step for producing the oxychloride. In accordance with the preferred aspect of the present invention, the dilute aqueous hydrogen chloride stream which is concentrated by being employed for quenching the gas from the oxidizer, is obtained from the effluent from the chlorination reactor.

The invention will be further described with respect to an embodiment thereof illustrated in the accompanying drawing, wherein:

The drawing is a simplified schematic flow diagram of an embodiment of the present invention as applied to a process for producing chlorinated hydrocarbons by the use of molten salts.

It is to be understood, however, that the scope of the overall invention is not to be limited by the hereinafter described preferred embodiment.

Referring now to the drawing, a molten chloride salt, such as a mixture of potassium chloride, cupric and cuprous chloride, in line 10, is introduced into the top of an oxidation reactor 11. A compressed oxygen containing gas in line 12, an aqueous solution of hydrogen chloride in line 13, obtained as hereinafer described, and a by-product combustion effluent, in line 14, comprising chlorine and/or hydrogen chloride, as well as carbon oxides, water vapor, nitrogen and perhaps unreacted oxygen, obtained as hereinafter described, are introduced into reactor 11. Reactor 11 is operated at a temperature of from about 600° to about 900° F, and at a pressure in the order of about 1 to 20 atmospheres. As a result of the countercurrent contact between the various feeds and the descending molten salt mixture, the salt is oxidized to produce copper oxychloride, and the hydrogen chloride and/or chlorine introduced with the combustion effluent and the hydrogen chloride introduced as aqueous hydrogen chloride are absorbed by the molten salt to produce cupric chloride. In addition, the water introduced with the aqueous hydrogen chloride is vaporized.

An effluent gas, including water vapor, nitrogen, carbon oxides and unabsorbed hydrogen chloride, and some chlorine, rises into the top of vessel 11 wherein the effluent gas is combined with lift gas, as hereinafter described, introduced through line 15. The combined gas is directly contacted in the top of vessel 11 with a spray of aqueous hydrogen chloride quench liquid, introduced through line 16 to cool the combined gas and eliminate any vaporized and entrained salts therefrom. The effluent gas is cooled to a temperature at which the molten salt is still in the form of a melt to permit the molten salt to flow back into the reactor 11.

The partially cooled gaseous stream withdrawn from reactor 11, through line 17, is directly quenched with aqueous hydrogen chloride, introduced through line 18, obtained as hereinafter described, and aqueous hydrogen chloride introduced through line 19 to effect cooling thereof to a temperature of from about 170° to about 250° F, as hereinabove described. As a result of such contact, the aqueous hydrogen chloride stream in line 18 is partially vaporized to produce a more concentrated aqueous hydrogen chloride solution.

A combined stream in line 21 is introduced into a vapor-liquid separation vessel, designated as 22, in order to separate aqueous hydrogen chloride from the remaining gas. The aqueous hydrogen chloride, withdrawn from vessel 22 through line 23 is cooled in cooler 24 and the cooled liquid in line 25 is passed through lines 16 and 19 for effecting quenching, as hereinabove described. The net aqueous hydrogen chloride solution recovered from separation 22 is introduced into reactor 11 through line 103.

The remaining gas withdrawn from vessel 22 through line 26 generally contains essentially all of the hydrogen chloride present in the effluent withdrawn from reactor 11, is introduced into a reactor 101, which contains a bed of activated carbon wherein chlorine present in the gas is converted to hydrogen chloride. Such a procedure is more fully described in U.S. application Ser. No. 656,769, filed on Feb. 10, 1976, now U.S. Pat. No. 4,036,776, and assigned to the same assignee. Alternatively, the gas could be passed directly to the absorption tower for hydrogen chloride recovery, in which case, the vent gas will contain chlorine The gas in line 30 is introduced into a hydrogen chloride absorption column, generally indicated as 27, wherein the gas is directly contacted with water, introduced through line 28, to effect absorption of the hydrogen chloride present in the gas. As hereinabove described, the absorption tower 27 is operated at a gas outlet temperature from about 170° to about 250° F, and a pressure from about 1 to about 20, and the water introduced through line 28, is introduçed in a quantity to effect absorption of hydrogen chloride and provide an aqueous hydrogen chloride stream having a hydrogen chloride concentration of from about 10% to about 20%, by weight. In addition, the gas which is withdrawn from the absorber contains no more than about 0.01 mole % of hydrogen chloride. Furthermore, such hydrogen chloride absorption is effected without any essential condensation of water vapor from the gas feed.

The aqueous hydrogen chloride, withdrawn from absorber 27, is recycled to the oxidizer through line 13 for recovery of the chlorine values thereof.

A gas stream is withdrawn from absorber 27 through line 31 and any hydrogen chloride present in the gas is neutralized by the addition of a suitable base through line 32. In accordance with a preferred aspect of the present invention, the base provided through line 32 is a waste aqueous stream containing sodium bicarbonate generated as a waste water stream in the recovery section for the effluent from the oxychlorination and/or chlorination reactor. The neutralization is effected in a manner to minimize the temperature reduction of the gas and water vapor condensation, whereby water produced in the oxidizer can be vented to the atmosphere as a gas.

The neutralized stream in line 33 is combined with any water in line 34, as hereinafter described, and the combined stream in line 35 introduced into a vapor-liquid separation vessel 36 to separate the aqueous stream from the remaining gas. The separated liquid is withdrawn, as a waste liquid through line 37. The gas stream is withdrawn from separator 36 through line 38 and a first portion thereof vented to the atmosphere through line 39. In accordance with the preferred aspect of the invention, the net water make of reactor 11 as well as the water evaporated from dilute aqueous hydrogen chloride stream 18 is vented to the atmosphere as a gas, thereby reducing waste water treatment.

The remainder of the gas stream in line 41 is cooled in cooler 42, to separate water therefrom prior to circulation of the gas to a compressor for ultimate use as a lift gas. The cooled stream in line 43 is introduced into a vapor-liquid separator 44. The separated water is withdrawn from vessel 44 through line 45 and is employed, in the appropriate amount, in line 28 for absorbing hydrogen chloride. Water withdrawn from vessel 44 through line 45, which is an excess of the amount required for meeting the absorption requirements, is circulated through line 34 for ultimate removal from the process through line 37.

The gas withdrawn from vessel 44 through line 46 is compressed in compressor 47, and the temperatures thereof regulated in heat exchanger 48, prior to passage through line 49 and 51, for use as lift gas for transporting molten salt, as hereinafter described.

The molten salt, now containing copper oxychloride and enriched in cupric chloride, is withdrawn from the bottom of vessel 11 through line 52, and lifted by the lift gas in line 51 into a separation vessel 53, positioned adjacent to the top of a chlorination and/or oxychlorination reactor 54. In separator 53, the molten salt is separated from the lift gas, with the molten salt being introduced into the top of reactor 54 through line 55. The lift gas is withdrawn from vessel 53, through line 56, and combined with lift gas used for transporting salt to the oxidation reactor 11, for introduction into the quenching portion of reactor 11, through line 15.

Fresh feed chlorine and/or hydrogen chloride is introduced into reactor 54 through unit 61, and fresh hydrocarbon feed, such as methane, is introduced through line 62. Recycled components such as unreacted methane and chlorinated methane intermediates, are introduced into reactor 54 through line 63. Reactor 54 is operated at temperatures of from about 600° to about 900° F, and at a pressure from about 1 to 20 atmospheres. As a result of the countercurrent contact between the molten salt mixture and the feed, the methane is chlorinated and/or oxychlorinated to chlorinated methanes.

An effluent gas is withdrawn from reactor 54 through line 64, and the effluent gas contains unreacted methane, chloromethanes, inerts, such as nitrogen and carbon monoxide, water vapor, carbon dioxide and hydrogen chloride. The effluent gas is introduced into a recovery section generally designated as 65 in order to separate and recover the various components thereof. Chlorinated methane product is withdrawn from recovery section 65 through line 66, and recycled components are withdrawn through line 63 for introduction into reactor 64.

In recovery section 65, hydrogen chloride is recovered from the gaseous effluent as an aqueous hydrogen chloride stream. In general, the aqueous hydrogen chloride is recovered by cooling the effluent to condense aqueous hydrogen chloride therefrom, with the aqueous hydrogen chloride generally having a hydrogen chloride concentration of no greater than 8%, generally in the order of from 1 to 6%. The condensed aqueous hydrogen chloride is withdrawn from the recovery section 65 through line 18, and employed for quenching the effluent in line 17, as hereinabove described. As a result, the aqueous hydrogen chloride is vaporized, with the hydrogen chloride ultimately being recovered and utilized in the process, as hereinabove described. In this manner, hydrogen chloride values are recovered from the oxychlorinator effluent without necessitating a separate aqueous hydrogen chloride concentration step.

Chlorinated hydrocarbons not recovered as reaction product and/or recycled as intermediates are withdrawn from recovery section 65 through line 67 and introduced into a combustion zone 68 wherein the chlorinated hydrocarbons are burned with molecular oxygen, introduced through line 69. A combustion effluent is withdrawn from combustion zone 68 through line 14 for introduction into reactor 11 to thereby recover the chlorine values thereof, as hereinabove described.

Molten salt is withdrawn from reactor 54 through line 71, and lifted by lift gas in line 49 into a separation vessel 72. In separator 72, the molten salt is separated from the lift gas, and introduced through line 10 into reactor 11. Lift gas is withdrawn from separator 72 through line 73 and combined with the lift gas in line 56 for introduction into the top of reactor 11 through line 15.

Numerous modifications of the hereinabove described embodiment are possible within the scope of the present invention. Thus, for example, the cooling of the oxidizer effluent in line 17 may be effected by other than direct contact quenching. Furthermore, aqueous hydrogen chloride recovered from the oxychlorinator effluent need not be employed as a quenching liquid.

It is also to be understood that the hereinabove described embodiment is also applicable to the production of other chlorinated hydrocarbons. In particular, the embodiment is applicable to the production of $C_2$ chlorinated hydrocarbons employing ethane and/or ethylene, as fresh feed.

The invention will be further described with respect to the following example; however, the scope of the invention is not to be limited thereby:

EXAMPLE

For a 250,000,000 chloromethane plant the stripped dilute HCl solution in line 18 from the chlorination section amounts to 16,600 lb/hr containing 900 lb/hr of HCl. This dilute HCl solution (5.4 wt. %) is used as a part of quench liquid in the quench line 21 to separator 22 where it is concentrated to about 14 wt. %. Net concentrated HCl solution is introduced into oxidizer 11.

The oxidizer 11 top effluent is also quenched by a cooled recycle stream 19 which amounts to 440,000 lb/hr containing 14 wt. % HCl. The overhead vapor from the separator 22 has the following composition.

| Components | LB/HR |
|---|---|
| Noncondensables | 223,400 |
| Chlorine | 380 |
| HCl | 780 |
| Water | 29,120 |
| | 253,680 |

The above stream is usually passed through an activated carbon bed to convert the chlorine contained in the stream into HCl. The total HCl in the stream 30 after the converter is 1170 lb/hr. The stream 30 is fed to the HCl absorber 27 which is operated at 250° F and 60 psia and scrubbed with 7,000 lb/hr of water condensate from line 28. The amount of HCl leaving the top of the absorber 27 is less than 15 lb/hr.

The stream 13 from the bottom of the absorber is 8,250 lb/hr containing 1,155 lb/hr of HCl. This stream is sent to the oxidizer 11 where HCl is converted into metal chloride.

This example shows that 1,155 lb/hr of HCl is recovered and about 10,000 lb/hr of water is evaporated from the dilute aqueous HCl stream 18 by the heat in the effluent stream 17 from the oxidizer 11. As the water vaporized is vented to atmosphere through line 39 about 9 million Btu/hr of cooling is eliminated.

The present invention is particularly advantageous in that hydrogen chloride is recovered from the effluent from the molten salt oxidizer as an aqueous hydrogen chloride stream, which can be recycled to the oxidizer without concentration thereof. In addition, the recycling of the aqueous hydrogen chloride recovered from the oxychlorinator effluent, to the quenching section of the oxidizer, eliminates the necessity for a separate hydrogen chloride concentrator.

As a further advantage, the overall cooling duty and waste water stream treatment of the plant is reduced in that a major portion of the water vapor produced in the process is released to the atmosphere, as a gas.

These and other advantages should be apparent to those skilled in the art with the teachings herein.

Numerous modifications and variations of the present invention are possible in light of the above teachings and, therefore, within the scope of the appended claims, the invention may be practiced otherwise than as particularly described.

What is claimed is:

1. A process for recovering hydrogen chloride, comprising:
   (a) contacting in an oxychlorination reaction zone aqueous hydrogen chloride and gaseous molecular oxygen with a salt mixture comprising a multivalent metal chloride in its higher and lower valence state to produce a salt mixture enriched in the higher valent metal chloride;
   (b) withdrawing a gas containing hydrogen chloride and water vapor from the oxychlorination reaction zone;
   (c) cooling the gas to a temperature of from 170° to 250° F, at a pressure of from 1 to 20 atmospheres without condensation of aqueous hydrogen chloride from the gas;
   (d) contacting gas from Step (c) having hydrogen chloride and water vapor in an amount whereby condensation would provide an aqueous hydrogen chloride solution containing no greater than 8%, by weight, hydrogen chloride with water to absorb hydrogen chloride and provide a remaining gas having a hydrogen chloride concentration of no greater than 0.01 mole %, said contacting being effected at a gas outlet temperature of from 170° to 250° F, and a pressure of from 1 to 20 atmospheres without condensation of water vapor from the gas, said water being introduced in a quantity to provide an adsorbed aqueous hydrogen chloride solution having a hydrogen chloride concentration of from 10% to 20%, by weight;
   (e) passing absorbed aqueous hydrogen chloride solution to the oxychlorination reaction zone;
   (f) neutralizing the remaining gas at a temperature of from 170° to 250° F and at a pressure of from 1 to 20 atmospheres; and
   (g) venting a portion of the neutralized remaining gas at the temperature of from 170° to 250° F whereby water present in the gas and produced in the oxychlorination reaction zone is vented as water vapor.

2. The process of claim 1 wherein the gas outlet temperature is from 175° to 225° F.

3. The process of claim 2 and further comprising:
   cooling the unvented portion of the remaining gas to condense water vapor therefrom; and
   employing condensed water vapor for contacting the cooled gas to absorb hydrogen chloride.

4. A process for recovering hydrogen chloride, comprising:
   (a) containing in a first reaction zone a salt mixture comprising a multivalent metal chloride in its higher and lower valence state with gaseous molecular oxygen and an aqueous solution of hydrogen chloride to produce the corresponding oxychloride and enrich the higher valent metal chloride of the salt mixture;
   (b) recovering from the first reaction zone a gas, containing hydrogen chloride and water vapor;
   (c) cooling said gas to a temperature of from 170° to 250° F, at a pressure of from 1 to 20 atmospheres, said cooling being effected by direct contact with aqueous hydrogen chloride obtained from step (i), said aqueous hydrogen chloride having a hydrogen chloride concentration of no greater than 8 weight percent, said contacting resulting in partial vaporization of said aqueous hydrogen chloride to provide remaining aqueous hydrogen chloride having a hydrogen chloride concentration of from 10% to 20%, by weight, said cooling being effected without condensation of aqueous hydrogen chloride from the gas;
   (d) introducing said remaining aqueous hydrogen chloride into the first reaction zone as a portion of said aqueous solution of hydrogen chloride;

(e) contacting the gas from step (c) having hydrogen chloride and water vapor in an amount whereby condensation would provide an aqueous hydrogen chloride solution containing no greater than 8%, by weight, hydrogen chloride with water to absorb hydrogen chloride and provide a remaining gas having a hydrogen chloride concentration of no greater than 0.01 mole percent, said contacting being effected at a remaining gas outlet temperature of from 170° to 250° F, and a pressure of from 1 to 20 atmospheres without condensation of water vapor, said water being employed in a quantity to provide an absorbed aqueous hydrogen dhloride solution having a hydrogen chloride concentration of from 10% to 20%, by weight;

(f) introducing absorbed aqueous hydrogen chloride into the first reaction zone as a further portion of said aqueous solution of hydrogen chloride;

(g) contacting salt mixture from step (a) in a second reaction zone with a hydrocarbon and a member selected from the group consisting of chlorine, hydrogen chloride and mixtures thereof to produce a reaction effluent containing chlorinated hydrocarbon, water vapor and hydrogen chloride;

(h) recovering an aqueous hydrogen chloride stream from the effluent produced in the second reaction zone; and (i) passing said aqueous hydrogen chloride to step (c) to effect direct contact cooling of said gas.

5. The process of claim 1 and further comprising:
neutralizing the hydrogen chloride present in said remaining gas at a temperature of from 170° to 250° F; and
venting a portion of the remaining gas at the temperature of from 170° to 250° F to vent water produced in the first and second reaction zones as water vapor.

6. The process of claim 5 wherein the multivalent metal chloride is copper chloride.

7. The process of claim 6 wherein said remaining gas outlet temperature is from 175° to 225° F.

* * * * *